United States Patent [19]

Makino et al.

[11] Patent Number: 4,871,723
[45] Date of Patent: Oct. 3, 1989

[54] METHOD FOR TREATING PSORIASIS BY EXTERNALLY ADMINISTERING TO A PATIENT A PHARMACEUTICAL COMPOSITION CONTAINING ACTIVE-TYPE VITAMIN D

[75] Inventors: Yuji Makino; Yoshiki Suzuki, both of Hino; Takashi Aoyagi, Sapporo, all of Japan

[73] Assignee: Teijin, Limited, Osaka, Japan

[21] Appl. No.: 933,326

[22] Filed: Nov. 21, 1986

Related U.S. Application Data

[63] Continuation-in-part of Ser. No. 784,305, Oct. 4, 1985, abandoned.

[30] Foreign Application Priority Data

Oct. 8, 1984 [JP] Japan .................................. 59-209631
Jul. 25, 1985 [JP] Japan .................................. 60-162893

[51] Int. Cl.$^4$ ............................................. A61K 31/59
[52] U.S. Cl. ...................................................... 514/167
[58] Field of Search .......................................... 514/167

[56] References Cited

U.S. PATENT DOCUMENTS

| | | | |
|---|---|---|---|
| 3,981,996 | 9/1976 | Leigh | 514/167 |
| 4,230,701 | 10/1980 | Holick | 514/167 |
| 4,248,867 | 2/1981 | Ikushima | 514/167 |
| 4,308,264 | 12/1981 | Conway | 514/167 |
| 4,364,941 | 12/1982 | Kiyoki | 514/167 |
| 4,442,093 | 4/1984 | Maeda | 514/167 |
| 4,501,737 | 2/1985 | Yamato | 514/167 |
| 4,610,978 | 9/1986 | Dikstein | 514/167 |

FOREIGN PATENT DOCUMENTS

| | | | |
|---|---|---|---|
| 129003 | 12/1874 | European Pat. Off. | 514/167 |
| 2826527 | 4/1979 | Fed. Rep. of Germany | 514/167 |
| 2389377 | 1/1979 | France | 514/167 |

OTHER PUBLICATIONS

Makino et al, Chem Abs 105, 30074f (1986).
The Merck Index; 10th Edition (1983); p. 1436.
"Biological Activity of 1,24(R)–Dihydroxyvitamin $D_3$ and 1,24(S)–Dihydroxy Vitamin $D_3$ in the Rat (41396)", C. M. Smith et al., Proceedings of the Society for Experimental Biology and Medicine, 170, 53–58 (1982).

*Primary Examiner*—Mark Berch
*Attorney, Agent, or Firm*—Wenderoth, Lind & Ponack

[57] ABSTRACT

A process for treating psoriasis by externally applying to the skin of a warm-blooded animal a composition comprising:
(A) a pharmaceutically effective amount of an active-type vitamin $D_3$,
(B) a substantially water-free carrier containing the active-type vitamin $D_3$ dissolved or uniformly dispersed therein, and
(C) a solvent selected from fatty acid esters, higher alcohols with 10 or more carbons and propylene carbonate.

5 Claims, No Drawings

METHOD FOR TREATING PSORIASIS BY EXTERNALLY ADMINISTERING TO A PATIENT A PHARMACEUTICAL COMPOSITION CONTAINING ACTIVE-TYPE VITAMIN D

This application is a continuation-in-part of now abandoned application Ser. No. 784, 305, filed Oct. 4, 1985, now abandoned.

This invention relates to a method of externally applying to the skin of a warm-blooded animal, a pharmaceutical composition for external use containing active-type vitamin $D_3$.

Active-type vitamins $D_3$ such as $1\alpha,25$-dihydroxycholecalciferol, $1\alpha,24$-dihydroxycholecalciferol and $1\alpha$-hydroxycholecalciferol are hormones which promote absorption and transportation of calcium in the small intestine, regulate bone absorption and bone resorption in bones and suppress secretion of parathyroid hormone in the parathyroid (U.S. Pat. Nos. 3,901,928 and 4,022,891 and Tetrahedron Letters, 40, 4147, 1972). Hence, the active type vitamins $D_3$ are used for the treatment of renal failure and osteomalacia in which active-type vitamins $D_3$ are insufficient and absorption of calcium is reduced, osteoporosis which is a disease associated with abnormal bone metabolism, and rickets showing the insufficiency of vitamin $D_3$ (Basic Research and Its Clinical Applications, 1099–1106, 1979).

Recently, new pharmacological activities of the active-type vitamins $D_3$ were found, and the possibility of using them as therapeutic agents for not only various diseases induced by abnormal metabolism of calcium but other diseases excepting bone disease has been studied.

Japanese Laid-Open Patent Publication No. 26820/1981 suggests the usability of active-type vitamin $D_3$ as an agent for suppressing immune function, for example as an agent for treating articular rheumatism.

Japanese Laid-Open Patent Publication No. 149224/1982 suggests the usability of active-type vitamin $D_3$ as an agent for inducing differentiation of cancer cells. It suggests that active-type vitamins $D_3$ promote differentiation of cancer cells at certain local sites of the cells and thus inhibit proliferation of the cancer cells.

"Abstracts of Papers in the Third Meeting of the Japanese Society of Bone and Mineral Metabolism" published by the Japanese Society of Bone and Mineral Metabolism on June 25, 1985, page 74 shows by clinical data that $1\alpha$-hydroxycholecalciferol and $1\alpha,25$-dihydroxycholecalciferol are effective for the treatment of psoriasis by oral administration and so is $1\alpha,25$-dihydroxycholecalciferol by external application (the Third Meeting of the Japanese Society of Bone and Mineral Metabolism was held for 2 days at Japan City Center on June 26 and 27, 1985).

European Laid-Open Patent Application No. 0123948 and the corresponding U.S. patent application Ser. No. 595,835 disclose a pharmaceutical composition for external use containing a glycerol ester of pyroglutamic acid as a drug penetration enhancer. This pharmaceutical composition can be applied to the skin or mucosa of a warm-blooded animal. Furthermore, since the above-mentioned glycerol ester can enhance penetration of various drugs through the skin or mucosa, the specifications of the above patent documents disclose the glycerol ester can be used as a penetration enhancer for various drugs such as anti-inflammatory agents, agents for the circulatory system, antimicrobial agent, anti-ulcer agents, analgesic agents, anticancer agents, antiemetic agents, anti-allergic agents, agents for the central nervous system, agents for the peripheral nervous system, biologicals and agents for the metabolic system. In addition, the above specifications give several examples of active-type vitamin $D_3$ as the agents for the metabolic system. Example 132 of these documents discloses an ointment comprising $1\alpha$-hydroxycholecalciferol as a drug and the above glycerol ester as the penetration enhancer. However, these specifications fail to describe anything on the usability of this composition for the treatment of articular rheumatism, cancer or psoriasis.

The specification of European Patent Application No. 85111034.6 (filed on September 2, 1985) discloses alkyl or alkenyl esters of pyroglutamic acid as penetration enhancers effective for many drugs similar to those described in the specification of European Laid-Open Patent Application No. 0123948. European Patent Application No. 85111034.6 does not give an example of a specific composition comprising active-type vitamin $D_3$ nor describe anything on the usability of such a composition for the treatment of articular rheumatism, etc.

It is an object of this invention to provide a pharmaceutical composition for external use comprising active-type vitamin $D_3$ and particularly the use of such composition for treating psoriasis.

Another object of this invention is to provide a stable pharmaceutical composition for external use comprising active-type vitamin $D_3$ in which the active-type vitamin $D_3$ can be protected from decomposition by water or moisture during formulation or storage.

Still another object of this invention is to provide a pharmaceutical composition for external use comprising active-type vitamin $D_3$ in which the concentration of the active-type vitamin $D_3$ at a local site is increased and maintained high for an extended period of time.

Yet another object of this invention is to provide a pharmaceutical composition for external use comprising active-type vitamin $D_3$ in which the concentration of the active-type vitamin $D_3$ at a local site is rendered high, whereas the amount of the vitamin $D_3$ to be circulated through the body is reduced to increase its bioavailability and avoid its side-effects such as hypercalcemia.

A further object of this invention is to provide a pharmaceutical composition for external use comprising active-type vitamin $D_3$ which can improve articular rheumatism efficiently when applied to the skin near the site of that disease, A still further object of this invention is to provide a pharmaceutical composition for external use comprising active-type vitamin $D_3$ which is effective with very good efficiency, for the improvement and disappearance of a pooriatic site of the skin by direct application thereto.

Other objects of this invention along with its advantages will be apparent from the following description.

According to this invention, these objects and advantages are achieved by a pharmaceutical composition for external application to the skin of a warm-blooded animal comprising (A) a pharmaceutically effective amount of an active-type vitamin $D_3$, and
(B) a substantially water-free carrier containing the active-type vitamin $D_3$ dissolved or uniformly dispersed therein.

Examples of the active-type vitamin $D_3$ used in this invention include
1α-hydroxycholecalciferol,
1α,25-dihydroxycholecalciferol,
1α,24-dihydroxycholecalciferol,
1α,24,25-trihydroxycholecalciferol,
1α-hydroxy-24-oxocholecalciferol,
1α,25-dihydroxy-24-oxocholecalciferol,
1α,25-dihydroxycholecalciferol-26,23-lactone,
1α,25-dihydroxycholecalciferol-26,23-peroxylactone,
26,26,26,27,27,27-hexafluoro-1α,25-dihydroxycholecalciferol,
25-hydroxycholecalciferol,
24-hydroxycholecalciferol,
24-oxocholecalciferol,
24,25-dihydroxycholecalciferol,
25-hydroxy-24-oxocholecalciferol,
25-hydroxycholecalciferol-26,23-lactone,
25-hydroxycholecalciferol-26,23-peroxylactone,
24-oxo-1α-hydroxy-$\Delta^{25}$-cholecalciferol,
1α,24(R)-dihydroxy-$\Delta^{25}$-cholecalciferol,
1α,24(S)-dihydroxy-$\Delta^{25}$-cholecalciferol,
26-chloro-24-oxo-1α-hydroxy-$\Delta^{25}$-cholecalciferol,
26-chloro-1α,24(R) dihydroxy-$\Delta^{25}$-cholecalciferol,
26-chloro-1α,24(S)-dihydroxy-$\Delta^{25}$-cholecalciferol,
24,24-difluoro-1α,25-dihydroxycholecalciferol,
26,26,26-trifluoro-1α,25-dihydroxycholecalciferol,
25-fluoro-1α,24(R)-dihydroxycholecalciferol, and
25-fluoro-1α,24(S)-dihydroxycholecalciferol.

Preferred among the above-exemplified active-type vitamin $D_3$ are 1α-hydroxycholecalciferol (to be sometimes written as 1α-OH-$D_3$ for short), 1α,25-dihydroxycholecalciferol [1α,25-$(OH)_2$-$D_3$ for short], 1α,24-dihydroxy-cholecalciferol [1α,24-$(OH)_2$-$D_3$ for short], 1α,24,25-trihydroxycholecalciferol [1α,24,25-$(OH)_2$-$D_3$ for short], 25-hydroxycholecalciferol (25-OH-$D_3$ for short), 24-hydroxycholecalciferol (24-OH-$D_3$ for short), 24,25-dihydroxycholecalciferol [24,25-$(OH)_2$-$D_3$ for short], 26-chloro24(R)-dihydroxycholecalciferol, 24,24-difluoro-1α,25dihydroxycholecalciferol and 26,26,26,27,27,27-hexafluoro25-dihydroxycholecalciferol. Of these, 1α,24-$(OH)_2$-$D_3$, 25-OH , 1α-OH-$D_3$, 26-chloro-1α,24(R)-dihydroxycholecalciferol, 24,24-difluoro-1α,25-dihydroxycholecalciferol and 26,26,26,27,27,27-hexafluoro-1α,25-dihydroxycholecalciferol are especially preferred.

Those active-type vitamin $D_3$ which have an asymmetric carbon atom, such as 1α,24-$(OH)_2$-$D_3$, can be used not only as an optically inactive compound but also as an optically active compound.

The above active-type vitamins $D_3$ used in this invention are known compounds and can be chemically synthesized easily, for example by the methods described in J. Amer. Chem. Soc., 95, 2748 (1973), Chem. Pharm. Bull., 21, 2568 (1978) and U.S. Pat. No. 4,022,891.

It is natural that the active-type vitamin $D_3$ should be contained in a pharmaceutically effective amount in the composition of this invention. For example, it is contained in an amount of 1 ng to 2 mg per gram of the carrier (B) to be described.

The carrier (B) used in the composition of this invention contains the active-type vitamin $D_3$ (A) dissolved or uniformly dispersed therein, and does not substantially contain water. To the best of the knowledge of the present inventors, there has been no literature reference which reports the susceptibility of active-type vitamins $D_3$ to decomposition by water or moisture. The present inventors have unexpectedly learned by experiments that the presence of water in a composition containing an active-type vitamin $D_3$ in a very low concentration causes decomposition of the active-type vitamin $D_3$ within a very short period of time and consequently the vitamin $D_3$ loses its activity.

Accordingly, the composition itself of the present invention may contain water, but the carrier containing the active-type vitamin $D_3$ dissolved or uniformly dispersed therein should not substantially contain water. For example, a composition prepared by dissolving the active-type vitamin $D_3$ in a water-insoluble oil, and emulsifying the solution in water to form an oil-in-water emulsion is within the scope of the composition of this invention since substantially no water exists in the carrier oil containing the vitamin $D_3$ although the composition itself contains water.

Accordingly, what is important in the composition of this invention is not whether it contains water or not but whether the carrier containing the active-type vitamin $D_3$ dissolved or uniformly dispersed therein substantially contains water or not. Hence, in the composition of this invention, the carrier itself may be hydrophilic or oleophilic. When a hydrophilic carrier is used, it is necessary to ensure that the composition does not contain water, and during formulation or storage, the composition is isolated from water or moisture.

Preferred carriers used in the composition of this invention are substantially water-immiscible. Examples are hydrocarbons, silicones, higher alcohols, sterols, sterol esters, higher fatty acids, fatty acid esters particularly higher fatty acid esters, fatty acid triglycerides, pressure-sensitive adhesive acrylic polymers, and mixtures of these.

The hydrocarbons are preferably selected from the group consisting of white vaseline, yellow vaseline, paraffins (hard paraffins liquid paraffins and paraffin waxes), microcrystalline waxes, polyethylene, squalane, squalene, etc.

Polydimethylsiloxane is a preferred example of the silicones.

The higher alcohols are preferably selected from the group consisting of myristyl alcohol, lauryl alcohol, cetyl alcohol, stearyl alcohol, cetostearyl alcohol, oleyl alcohol, anethole, citronellol, eugenol, etc.

The sterols or sterol esters are preferably selected from the group consisting of lanolin, liquid lanolin, lanolin wax, isopropyl lanolin, acetylated lanolin, lanolin alcohol, cholesterol, etc.

The fatty acids are selected preferably from the group consisting of lauric acid, myristic acid, palmitic acid, stearic acid, oleic acid, etc.

The higher fatty acid esters are preferably selected from the group consisting of carnauba wax, beeswax, jojoba wax, spermaceti wax, polyethylene glycol ester, ethylene glycol ester, glycerin monoesters, sorbitol esters, sorbitan esters, isopropyl myristate, isopropyl palmitate, isopropyl adipate, hexyl laurate, diisopropyl adipate, decyl oleate, diethyl sebacate, isopropyl myristate, triacetine, glycerin tricaproate, glycerin tricaprylate, glycerin tricaprate, glycerin trilaurate, glycerin trilinoleate propylene glycol dipelargonate and propylene glycol dicaprate etc.

The fatty acid glycerides are selected preferably from the group consisting of almond oil, corn oil, cotton seed oil, olive oil, soybean oil, peanut oil, coconut oil, fractionated coconut oil, sesame oil, etc.

Polyhydric alcohols such as propylene glycol and glycerin can also be used as the carrier.

The pressure-sensitive adhesive acrylic polymers are preferably those comprising $C_4$-$C_{12}$ alkyl esters of acrylic or methacrylic acid, such as butyl acrylate, 2-ethylhexyl acrylate or octyl acrylate, as a major component.

The composition of this invention may further include a chemical component different from the carrier, for example a structural matrix agent such as colloidal silica, bentonite or montmorillonite; an antioxidant such as butylated hydroxyanisole (BHA), butylated hydroxytoluene (BHT), propyl gallate, pyrogallol, hydroxyquinone, hydroxycoumarin and tocopherols; an antiseptic such as phenol, cresol, parabens, benzyl alcohol, sorbic acid and quaternary ammonium compound; an absorption promoter selected from the group consisting of propylene glycol, oleic acid, urea, higher fatty acid esters of sucrose, diisopropyl adipate, diethyl sebacate, isopropyl myristate, hexyl laurate, dimethyl sulfoxide and mixtures of these; and a coloring agent such as 9-ortho-carboxyphenyl-6-hydroxy-2,4,5,7-tetraiodo-3-isoxanthone disodium salt, disodium 1-para-sulfophenylazo-2-naphthol-6-sulfonate, and 4-{[4-(N-ethyl-meta-sulfobenzylamino)-phenyl]-(2-sulfoniumphenyl)-methylene}-[1-((N-ethyl-meta-sulfobenzyl)-$\Delta^{2,5}$cyclohexadieneimine]disodium salt.

The pharmaceutical composition of this invention may be applied in various forms to the skin of a warm blooded animal. For example, it may be used as a liquid or semisolid such as a solution, an ointment, a gel ointment, a cream or a lotion. When the pressure-sensitive adhesive polymer is used as a carrier, the composition of this invention may be used in a form uniformly spread and supported on the surface of a lined support.

The composition of this invention which is liquid or semisolid may be formed into a solution, ointment or gel ointment containing substantially no water, or an ointment, cream or lotion containing a substantial amount of water. These compositions may be prepared by properly selecting the carrier. For example, the composition of this invention in solution form may be prepared by dissolving the active-type vitamin $D_3$ in at least one of squalane, liquid paraffin, squalene, liquid lanolin, citronellol, isopropyl palmitate, diisopropyul adipate, a vegetable oil, ethanol, glycerol, propylene glycol, etc. Compositions containing hydrophilic carriers should be isolated from moisture during preparation and storage.

The composition in the form of an ointment (anhydrous) may be prepared, for example, as an ointment comprising the active-type vitamin $D_3$ and a mixture of white vaseline and diisopropyl adipate (mixing ratio 4:1), a simple ointment comprising the active-type vitamin $D_3$, beeswax and a vegetable oil, or a paraffin ointment comprising the activated vitamin $D_3$, bleached beeswax, a solid paraffin, cetostearyl alcohol and vaseline.

The gel ointment may be prepared by uniformly dissolving the active-type vitamin $D_3$ in a gel composed of a vegetable oil such as fractionated coconut oil and a structural matrix agent such as bentonite.

The cream may be prepared as a W/O cream from the activated type vitamin $D_3$, dehydrated lanolin, stearyl alcohol, isopropyl myristate, cetorimide and water.

The lotion may be prepared as an emulsion-type lotion comprising a mixture of the active-type vitamin $D_3$, bleached beeswax, cetanol, sodium laurylsulfate, glycerin and water, or an emulsion-type lotion comprising the active-type vitamin $D_3$, stearyl alcohol, liquid paraffin, sodium laurylsulfate, methyl p-hydroxybenzoate, propyl p-hydroxybenzoate and water.

When the composition of this invention is used in a form uniformly spread on a lined support, it is possible, for example, to dissolve the active-type vitamin $D_3$ in at least one liquid carrier of the types described above to form a solution or a semisolid, apply the solution or semisolid to a laminate composed of a lined support and a porous pressure-sensitive adhesive layer, and fill it into the micropores of the adhesive layer. Alternatively, the active-type vitamin $D_3$ and the pressure-sensitive adhesive polymer in a suitable solvent, and the solution is uniformly spread on the surface of a lined support, followed by removing the solvent.

The pressure-sensitive adhesive polymer may, for example, be an acrylic pressure-sensitive adhesive, a rubber-type pressure-sensitive adhesive, or a silicone-type pressure-sensitive adhesive. Illustrative of the support are a polyethylene film and an ethylene/vinyl acetate copolymer film.

The pharmaceutical composition for external use provided by this invention are suitable for the treatment of articular rheumatism, cancer (e.g., skin cancer or uterus cancer), and various types of psoriasis such as psoriasis vulgaris, pustular psoriasis, guttate psoriasis and erythroderma-type psoriasis.

The amount of the pharmaceutical composition to be administered varies depending upon the type of the disease of a patient, the severity of the disease, the type of the active-type vitamin $D_3$, etc. For example, when a composition comprising the active-type vitamin $D_3$ in a concentration of 200 to 0.1 microgram/g is preferably administered two times a day by simple coating and rubbing, or once a day by an occluding method.

The following Examples illustrate the present invention in more detail.

EXAMPLE 1

Ointments of $1\alpha,25$-$(OH)_2$-$D_3$ and $1\alpha$-OH-$D_3$ Purified water was added to 25 g of white vaseline, 22 g of stearyl alcohol, 12 g of propylene glycol, 1.5 g of sodium laurylsulfate, 0.025 of ethyl p-hydroxybenzoate and 0.013 g of propyl p-hydroxybenzoate to prepare 100 g of a hydrophilic ointment. To 99 g of the hydrophilic ointment, a solution of 0.5 mg of $1\alpha$-OH-$D_3$ or 0.5 mg of $1\alpha,25$-$(OH)_2$-$D_3$ in 1 g of propylene glycol, and they were well kneaded to obtain an ointment (1 g of the ointment contained 5 micrograms of $1\alpha$-OH-$D_3$ or $1\alpha,25$-$(OH)_2$-$D_3$.

(ii) Hair was removed from the femoral parts of five male Wistar-strain rats (body weight 220 to 230 g), and 100 mg of the ointment prepared in (i) was well rubbed into the hair-removed part of each animal. Two hours later, the rats were sacrificed, and the skin at the ointment-administered site was carefully removed and the muscles inside were taken out. The amount of $1\alpha,25$-$(OH)_2$-$D_3$ or $1\alpha$-OH-$D_3$ in the muscles was determined by binding protein assay for the former and radioimmunoassay for the latter.

As a control, 0.5 microgram of $1\alpha,25$-$(OH)_2$-$D_3$ or $1\alpha$-OH-$D_3$ was orally administered to five rats [$1\alpha,2$-$5(OH)_2$-$D_3$ or $1\alpha$-OH-$D_3$ was prepared as a 0.2% Triton X-100 solution in a concentration of 1.25 micrograms/ml, and 500 microliters of the solution was administered). The rats in the control group were likewise sacrificed 2 hours later, and in the same way as above, the amount of $1\alpha,25\text{-(OH)}_2\text{-D}_3$ or $1\alpha\text{-OH-D}$ in the femoral muscles was measured.

The amounts of the $1\alpha,25\text{-(OH}$ and $1\alpha\text{-OH-D}_3$ in the femoral muscles of the rats in the ointment-applied group and the control group are shown in Table 1.

TABLE 1

|  |  | Amounts in the femoral muscles | | |
|---|---|---|---|---|
|  |  | 1st time (5 rats) | 2nd time (5 rats) | 3rd time (5 rats) |
| Ointment-applied group | $1\alpha,25\text{-(OH)}_2\text{-D}_3$ | 396 | 505 | 517 |
|  | $1\alpha\text{-OH-D}_3$ | 441 | 607 | 588 |
| Control group | $1\alpha,25\text{-(OH)}_2\text{-D}_3$ | 89 | 113 | 104 |
|  | $1\alpha\text{-OH-D}_3$ | 103 | 98 | 126 |

EXAMPLE 2

Ointment of $1\alpha,24(R)\text{-(OH)}_2\text{-D}_3$ (i) A suitable amount of $1\alpha,24(R)$-dihydroxycholecalciferol was dissolved in diisopropyl adipate, and the solution was uniformly mixed with white vaseline to form an ointment. The mixing ratio of diisopropyl adipate to white vaseline was always maintained at 1:4 by weight, and the concentration of $1\alpha,24(R)$-dihydroxycholecalciferol in the ointment was adjusted to 400 micrograms/30 mg, 40 micrograms/30 mg, and 4 micrograms/30 mg.

(ii) Each of the three ointment thus prepared was applied to the site of psoriasis vulgaris of a 28-year old woman, and their therapeutic effects were evaluated. Specifically, ±he ointment having a $1\alpha,24(R)\text{-(OH)}_2\text{-D}_3$ concentration of 400 micrograms/30 mg was applied twice daily each in an amount of 30 mg to psoriasis vulgaris at the lower part of the right femur (diseased part A). The ointment having a $1\alpha,24(R)\text{-(OH)}_2\text{-D}_3$ concentration of 40 micrograms/30 g was applied twice a day each in an amount of 30 mg to psoriasis vulgaris at the lower part of the left femur (diseased part B). The ointment having a $1\alpha,24(R)\text{-(OH}$ concentration of 4 micrograms/30 mg was applied twice a day each in an amount of 30 mg to psoriasis vulgaris at the middle part of the right femur (the diseased part C).

The therapeutic effects were evaluated on a scale of 5 grades as follows:

| Degree of severity |
|---|
| 4: very serious |
| 3: serious |
| 2: medium |
| 1: light |
| 0: disappeared |
| 1. (erythema 4-0) |
| 2. (scale 4-0) |
| 3. (infiltration 4-0) |
| 4. (papula 4-0) |

The diseased parts A to C originally had a degree of severity of 4. Five days after the beginning of treatment, an improvement was observed in all cases (severity Ten days later, all cases were cured (severity 0). Upon curing, the administration of the drug was stopped, and thereafter, the conditions of the diseased parts were periodically observed.

In the diseased parts A to C to which $1\alpha,24(R)$-dihydroxycholecalciferol was applied, no relapse of lesion was noted after more than 30 days from the stopping of the drug application.

The above results show that the $1\alpha,24(R)$-di-hydroxycholecalciferol had a good therapeutic effect on psoriasis vulgaris.

EXAMPLE 3

Cream of $1\alpha,25\text{-(OH)}_2\text{-D}_3$

Twenty grams of glycerin monostearate and 4 g of polyoxyethylene glycerin palmitate were taken and stirred over a water bath kept at 60° C. To the mixture were added 0.5 mg of $1\alpha,25\text{-(OH)}_2\text{-D}_3$ and 0.2 g of butyl hydroxytoluene, and they were well mixed. Methyl p-hydroxybenzoate (0.15 g) was dissolved in about 60 ml of purified water, and 7 g of glycerol was added. To the aqueous solution, the oil layer prepared above was added little by little, and they were well stirred. A small amount of purified water was added to adjust the total amount of the resulting cream to 100 g.

EXAMPLE 4

Ointment of $1\alpha,24(R)\text{-(OH)}_2\text{-D}_3$

One milligram of $1\alpha,24(R)$-dihydroxycholecalciferol was dissolved in 50 g of diisopropyl adipate. The solution was mixed with 950 g of white vaseline to obtain an ointment (the concentration of $1\alpha,24(R)$-dihydroxycholecalciferol: 1 microgram/g).

EXAMPLE 5

One milligram of $1\alpha,25$-dihydroxycholecalciferol was dissolved in 670 g of olive oil. The solution was mixed with 330 g of beeswax in the molten state, and with stirring, the mixture was gradually cooled to obtain an ointment (the concentration of $1\alpha,25$-dihydroxycholecalciferol: 1 microgram/g).

EXAMPLE 6

W/O emulsion-type ointment of $1\alpha\text{-OH-D}_3$

One milligram of 1 -hydroxycholecalciferol, 400 g of white vaseline, 180 g of cetanol, 50 g of sorbitan sesquioleate, 5 g of lauromacrogol, 1 g of ethyl p-hydroxybenzoate, 1 g of butyl p-hydroxybenzoate and 363 g of purified water were mixed to prepare a W/O emulsion-type ointment (the concentration of $1\alpha$-hydroxycholecalciferol: 1 microgram/g).

EXAMPLE 7

One milligram of $1\alpha,25$-dihydroxycholecalciferol, 250 g of white vaseline, 220 g of stearyl alcohol, 120 g of propylene glycol, 15 g of sodium laurylsulfate, 0.25 g of ethyl p-hydroxybenzoate, 0.15 g of propyl p-hydroxybenzoate and 393 g of purified water were mixed to form an O/W emulsion-type ointment (the concentration of $1\alpha,25$-dihydroxycholecalciferol: 1 microgram/g).

EXAMPLE 8

W/O emulsion-type cream of $1\alpha,24\text{-(OH)}_2\text{-D}_3$

One milligram of $1\alpha,24(R)$-dihydroxycholecalciferol, 350 g of lanolin, 190 g of stearyl alcohol, 50 g of isopropyl myristate, 50 g of cetorimide and 360 g of purified water were mixed to form a W/O emulsion-type cream (the concentration of $1\alpha,24$-dihydroxycholecalciferol: 1 microgram/g).

EXAMPLE 9

One milligram of 1α,24(R)-dihydroxycholecalciferol was well mixed with 1,000 g of Plastibase to prepare an ointment (the concentration of 1α,24(R)-dihydroxycholecalciferol: 1 microgram/g).

EXAMPLE 10

One milligram of 1α,24(R)-dihydroxycholecalciferol was dissolved in 700 g of propylene glycol. The solution was added with good stirring to a solution prepared by mixing 250 g of stearyl alcohol and 50 g of stearic acid and heating the mixture to 80° to 85° C. The mixture was cooled to room temperature to form an ointment (the concentration of 1α,24(R)-dihydroxycholecalciferol: 1 microgram/g).

EXAMPLE 11

One mg of 1α,24(R)-dihydroxycholecalciferol was dissolved in 40 g of propylene carbonate. The solution was added to 840 g of fractionated coconut oil (Miglyol 812 ®, a product of Dynamit Nobel Company), and the mixture was stirred. Then, with stirring, 120 g of bentonite was added and well mixed to form a gel ointment (the concentration of 1α,24(R)-dihydroxycholecalciferol: 1 microgram/g).

EXAMPLE 12

One mg of 1α,24(R)-dihydroxycholecalciferol was added to a co-melted mixture of 60 g of lanolin alcohol, 240 g of paraffin, 100 g of white vaseline and 600 g of liquid paraffin to prepare an ointment (the concentration of 1α,24(R)-dihydroxycholecalciferol: 1 microgram/g).

EXAMPLE 13

One milligram of 1α,24(R)-dihydroxycholecalciferol was added to a co-melted mixture of 500 g of white vaseline, 240 g of cetostearyl alcohol, 60 g of cetomacrogol and 200 g of liquid paraffin to prepare an ointment (the concentration of 1α,24(R)-dihydroxycholecalciferol: 1 microgram/g).

EXAMPLE 14

One milligram of 1α,24(R)-dihydroxycholecalciferol was added to a solution of 50 g of cetostearyl alcohol and 500 g of liquid paraffin. Then, a solution of 5 g of cetolimide in 455 ml of purified water was added, and with sufficient stirring, a cream was obtained (the concentration of 1α,24(R)-dihydroxycholecalciferol: 1 microgram/g).

EXAMPLE 15

One milligram of 1α,24(R)-dihydroxycholecalciferol was dissolved in 25 g of heated stearyl alcohol, and then 250 g of liquid paraffin was added. Separately, 0.25 g of methyl p-hydroxybenzoate, 0.15 g of propyl p-hydroxybenzoate, 10 g of sodium laurylsulfate, and 120 g of propylene glycol were dissolved in 595 g of purified water to prepare an aqueous solution. The aqueous solution was added to the oil phase prepared previously, and the mixture was stirred to prepare an emulsion-type lotion (the concentration of 1α,24(R)-dihydroxycholecalciferol: 1 microgram/g).

EXAMPLE 16

Ointment of 26-chloro-1α,24(R)-(OH)$_2$-D$_3$

One milligram of 26-chloro-1α,24-dihydroxycholecalciferol was dissolved in 50 mg of diisopropyl adipate. The solution was mixed with 950 g of white vaseline to prepare an ointment (the concentration of 26-chloro-1α,24(R)-dihydroxycholecalciferol: 1 microgram/g).

EXAMPLE 17

The drugs for external used prepared in Examples 4 to 15 were individually put into glass bottles. The bottles were sealed and stored at room temperature. The contents of 1α,24(R)-dihydroxycholecalciferol in the drugs were periodically measured by high performance liquid chromatography.

As a control, an ethanolic aqueous solution of 1α,24(R)-dihydroxycholecalciferol (ethanol:water=1:1 by volume; the concentration of 1α,24(R)-dihydroxycholecalciferol: 1 microgram/g) (Control Example 1), and a macrogol ointment of 1α,24(R)-dihydroxycholecalciferol (the concentration of 1α,24(R)-dihydroxycholecalciferol: 1 microgram/g; this ointment contained 2% by weight of water) (Control Example 2) were stored in the same way as above.

The results are shown in Table 2. The results show that the drugs of Examples 4 to 15 had better stability than the drugs of Control Examples.

TABLE 2

| Drugs | 10 days | 20 days | 30 days |
| --- | --- | --- | --- |
| Example 4 | 98 | 100 | 98 |
| Example 5 | 99 | 97 | 96 |
| Example 6 | 99 | 98 | 98 |
| Example 7 | 97 | 98 | 97 |
| Example 8 | 99 | 98 | 97 |
| Example 9 | 100 | 98 | 99 |
| Example 10 | 99 | 98 | 97 |
| Example 11 | 98 | 100 | 98 |
| Example 12 | 97 | 98 | 97 |
| Example 13 | 99 | 97 | 97 |
| Example 14 | 96 | 97 | 97 |
| Example 15 | 99 | 97 | 98 |
| Control Example 1 | 93 | 87 | 82 |
| Control Example 2 | 83 | 70 | 59 |

EXPERIMENT

EXAMPLE 18

0.1 mg of 1α,24-dihydroxycholecalciferol (1α,24-(OH)$_2$-D$_3$) was dissolved in 0.5 g of diisopropyl adipate. This solution was mixed under stirring with 99.5 g of white vaseline heated at 50° C. to make a homogenous composition. It was quenched to give a fat and oil ointment (concentration of 1α,24-(OH)$_2$-D$_3$ 1 microgram/g). In like manner ointments and creams were prepared and tested as 9 Controls. Procedures for their preparations in Controls will be described hereinafter:

CONTROL 3

Cream 20 g of glycerin monostearate and 4 g of polyoxyethylene glycerine palmitate were taken and stirred on a water bath with the temperature held at 60° C. 0.1 mg of 1α,24-(OH)$_2$-D$_3$ and 0.2 g of butyl hydroxytoluene were thoroughly admixed. 0.15 g of methyl p-hydroxybenzoate was dissolved in about 60 ml of purified water and 7 g of glycerin was added. This aqueous layer was thoroughly stirred by adding the previously-prepared oil layer in portions, and a small amount of purified water was added to make the total amount 100 g.

CONTROL 4

Hydrogel ointment 0.1 mg of $1\alpha,24\text{-(OH)}_2\text{-D}_3$ was dissolved in 40 g of ethanol and 10 g of propylene glycol. It was stirred by addition of a solution of 1 g of HIVISWAKO 104 ® swollen in 20 g of purified water. Then a solution of 1.1 g of diisopropanolamine in 10 g of purified water was further added and purified water was added until the total amount reached 100 g whereby a gel ointment was prepared.

CONTROL 5

Macrogol ointment (water-soluble base)

50 g of Macrogol 400 and 50 g of Macrogol 4,000 were dissolved on a water bath by heating at 60° C. and thoroughly stirred by addition of 0.1 mg of $1\alpha,24\text{-(OH)}_2\text{-D}_3$. After that it was quenched to make a macrogol ointment.

CONTROL 6

Lyogel ointment 0.1 mg of $1\alpha,24\text{-(OH)}_2\text{-D}_3$ was dissolved in 70 g of propylene glycol. This solution was added to 30 g of stearyl alcohol which turned the solution by heating at 60° C., thoroughly stirred and then quenched to make a lyogel ointment.

CONTROL 7

0.1 mg of $1\alpha,24\text{-(OH)}_2\text{-D}_3$ was added under stirring to 100 g of white vaseline heated at 50° C. to make a homogenous composition. It was quenched to give a fat and oil ointment.

CONTROL 8

0.1 mg of $1\alpha,24(R)\text{-(OH)}_2\text{-D}_3$ was dissolved in 30 g of almond oil. This solution was added under stirring to 70 g of white vaseline at 50° C. to make a homogenous composition. It was quenched to give a fat and oil ointment.

CONTROL 9

0.1 mg of $1\alpha,24(R)\text{-(OH)}_2\text{-D}_3$ was dissolved in 0.2 ml of ethyl alcohol. This solution was added under stirring to 100 g of white vaseline heated at 50° C. to make a homogenous composition. It was quenched to give a fat and oil ointment.

CONTROL 10

0.1 mg of $1\alpha,24(R)\text{-(OH)}_2\text{-D}_3$ was dissolved in 0.5 g of propylene glycol. This solution was added under stirring to 99.5 g white vaseline heated at 50° C. to make a homogenous composition. It was quenched to give an ointment.

CONTROL 11

0.1 mg of $1\alpha,24(R)\text{-(OH)}_2\text{-D}_3$ was dissolved in 0.5 g of squalane heated at 50° C. This solution was added under stirring to 99.5 g of white vaseline heated at 50° C. to make a homogenous composition. It was quenched to give a fat and oil ointment.

These preparations formulated in Example 16 and Controls 3-11 were preserved at room temperature to investigate the changings of residual percent of $1\alpha,24\text{-(OH)}_2\text{-D}_3$ with the lapse of time. The results were shown in Table 1. It is noted from this Table 1 that the preparations of Example 16 alone is stabilized over prolonged periods of time.

EXAMPLES 19-25

In like manner as used in Example 18 ointments comprising $1\alpha,24\text{-(OH)}_2\text{-D}_3$, diisopropyl adipate and white vaseline were prepared except that the amount of diisopropyl adipate used was varied. The ointments were observed for their appearances after they were preserved at room temperature for one year. The results were shown in Table 2.

EXAMPLES 26-34

In like manner as used in Example 18 fat and oil ointments were prepared using various solvents and fat and oil bases indicated in following Table A. The content of $1\alpha,24\text{-(OH)}_2\text{-D}_3$ was set at 1.0 milligram/g throughout the whole Examples and the content of the solvent 0.5% throughout the whole Examples.

TABLE A

| | Solvent | Fat and oil base |
|---|---|---|
| Example 26 | Decyl oleate | White vaseline |
| Example 27 | Diethyl sebacate | Polyethylene (5%) + Liquid paraffin (95%) |
| Example 28 | Triacetin | Yellow vaseline |
| Example 29 | Propylene carbonate | White vaseline (95%) + Liquid paraffin (5%) |
| Example 30 | Octyl dodecanol | White vaseline (95%) + Liquid paraffin (5%) |
| Example 31 | Hexadecyl alcohol | White vaseline (95%) + Liquid paraffin (5%) |
| Example 32 | Oleyl alcohol | White vaseline (95%) + Liquid paraffin (5%) |
| Example 33 | Propylene glycol dicaprylate | White vaseline (95%) + Liquid paraffin (5%) |
| Example 34 | Propylene glycol dicaprate | White vaseline (95%) + Liquid paraffin (5%) |

These respective ointments were preserved at room temperature for 6 months and for one year to investigate residual percent of $1\alpha,24\text{-(OH)}_2\text{-D}_3$. The investigation results were shown in following Table 3.

RESULTS AND OBSERVATIONS

Following Tables 3, 4 and 5 show term preservation stabilities of preparations formulated in said Examples and Controls.

TABLE 3

| | Residual percent (%) of $1\alpha,24\text{-(OH)}_2\text{-D}_3$ | | | |
|---|---|---|---|---|
| Preparation | 3 months | 6 months | 9 months | 12 months |
| Example 18 | 100 | 98 | 98 | 97 |
| Control 3 | 97 | 93 | 85 | 82 |
| Control 4 | 97 | 92 | 83 | 81 |
| Control 5 | 99 | 95 | 91 | 87 |
| Control 6 | 100 | 97 | 93 | 88 |
| Control 7 | 100 | 96 | 92 | 87 |
| Control 8 | 100 | 93 | 90 | 83 |
| Control 9 | 100 | 98 | 92 | 87 |
| Control 10 | 99 | 95 | 80 | (Note 1) 72 |
| Control 11 | 98 | 92 | 84 | 80 |

(Note 1) Phase separation was observed. Moisture absorption was also observed.

TABLE 4

| Ointment | Weight ratio (%) of diisopropyl adipate | Appearance after one year at room temperature |
| --- | --- | --- |
| Example 18 | 0.5 | Same as at the time of initiation |
| Example 19 | 0.1 | Same as at the time of initiation |
| Example 20 | 0.25 | Same as at the time of initiation |
| Example 21 | 1.0 | Same as at the time of initiation |
| Example 22 | 5.0 | Same as at the time of initiation |
| Example 23 | 10.0 | Same as at the time of initiation |
| Example 24 | 20.0 | Same as at the time of initiation |
| Example 25 | 25.0 | Same as at the time of initiation |
| Example 26 | 30.0 | Fluidized and turned to a liquid |

TABLE 5

| | Residual percent (%) of $1\alpha,24\text{-(DH)}_2\text{-D}_3$ | |
| --- | --- | --- |
| | After 6 months | After 12 months |
| Example 27 | 98 | 98 |
| Example 28 | 97 | 98 |
| Example 29 | 99 | 97 |
| Example 30 | 97 | 98 |
| Example 31 | 100 | 96 |
| Example 32 | 99 | 97 |
| Example 33 | 97 | 97 |
| Example 34 | 99 | 97 |
| Example 35 | 98 | 97 |

It follows from Tables 3, 4 and 5 above that a combination of a specified solvent and a specified oily carrier used in the ointments of the present invention alone can insure a long term preservation stability of $1\alpha,24\text{-(OH)}_2\text{-D}_3$. In other words, heretofore-well-known conventional solvents and carriers, as Controls 3–11 show, are lower in power capable of preserving the activity of $1\alpha,24\text{-(OH)}_2\text{-D}_3$.

What is claimed is:

1. A method for treating psoriasis, which comprises administering externally to a patient suffering from psoriasis an ointment consisting essentially of (A) an effective amount of 1α,24-dihydroxycholecalciferol, (B) a solvent selected from the group consisting of fatty acid esters, higher alcohols with 10 or more carbons and propylene carbonate and (C) an oily carrier selected from the group consisting of white vaseline, yellow vaseline and liquid paraffins.

2. The method of claim 1, wherein said effective amount of 1α,24-dihydroxycholecalciferol is 0.1 μg to 200 micrograms per gram of the sum of the solvent (B) and the oily carrier (C).

3. The method of claim 1, wherein the amount of the solvent (B) is 0.01 to 25% by weight of the ointment.

4. The method of claim 1, wherein the fatty acid esters are selected from the group consisting of diisopropyl adipate, decyl oleate, diethyl sebacate, isopropyl myristate, triacetine, glycerin tricaproate, glycerin tricaprylate, glycerin tricaprate, glycerin trilaurate, glycerin trilinoleate propylene glycol dipelargonate and propylene glycol dicaprate.

5. The method of claim 1, wherein the higher alcohols are selected from the group consisting of octyl dodecanol, hexadecyl alcohol and oleyl alcohol.

* * * * *